United States Patent [19]

Lanier et al.

[11] Patent Number: 5,124,251
[45] Date of Patent: Jun. 23, 1992

[54] CD3 ZETA CO-ASSOCIATED COMPLEX ON CD16⁻ NK CELLS

[75] Inventors: Lewis L. Lanier, Los Altos; Joseph H. Phillips, San Carlos, both of Calif.

[73] Assignee: Becton, Dickinson and Company, Franklin Lakes, N.J.

[21] Appl. No.: 472,988

[22] Filed: Jan. 31, 1990

[51] Int. Cl.⁵ .................. G01N 33/567; G01N 33/53; G01N 33/555
[52] U.S. Cl. .................. 435/7.21; 435/7.24; 436/547; 436/548
[58] Field of Search .............. 435/7.21, 7.24, 7.9, 435/70.21, 172.2, 240.27; 530/387; 436/547, 548

[56] References Cited

PUBLICATIONS

Allison et al., Ann. Rev. Immunol. 5:503-540, 1987.
Clevers et al., Eur. J. Immunol. 18:705-710, 1988.

*Primary Examiner*—Esther L. Kepplinger
*Assistant Examiner*—Donna C. Wortman
*Attorney, Agent, or Firm*—Robert M. Hallenbeck

[57] ABSTRACT

A novel protein complex is disclosed which is co-associated with CD3ζ on CD16⁻ NK cells. A purified form of the protein complex, a gene encoding the protein complex and method of producing the purified protein complex also are disclosed. Antibodies that bind to the protein complex and methods for their use further are disclosed.

7 Claims, 5 Drawing Sheets

CD3 ZETA CO-ASSOCIATED COMPLEX ON CD16⁻ NK CELLS

SUMMARY OF THE INVENTION

This invention relates to novel complex co associated with the CD3$\zeta$ protein on CD16⁻ NK cells, and more particularly relates to a purified form of the complex, a gene encoding the complex and monoclonal antibodies to the complex. Methods of using the monoclonal antibodies to detect cells bearing this novel complex also are disclosed.

BACKGROUND OF THE INVENTION

NK cells (or "Natural Killer" cells) are lymphoctyes found in the peripheral blood, in bone marrow and in other lymphoid tissues. NK cells are not considered to be T cells because they do not rearrange or productively transcribe the $\alpha$, $\beta$, $\gamma$ or $\delta$ genes of the T cell antigen receptor complex (or "TcR"). NK cells have ability to kill and lyse certain tumor and virally infected cells. Unlike T cells, however, the killing activity of these cells is not restricted by the major histocompatiblity complex (or "MHC"). NK cells also secrete interferons and cytokines that regulate immune responses and hematopoiesis.

Morphologically, NK cells usually are large granular lymphocytes with prominent azurophilic granules. NK cells also may be identified by the expression of certain markers or structures on their cell surface. These structures can be detected by monoclonal antibodies which have been prepared by conventional methods against them.

The prototypic structures (or "antigens") expressed by the majority of NK cells are CD16 and CD56. (The CD or "Cluster Designation" is an international standard used in the field to define a particular antigen by its molecular weight, cell type distribution and other criteria. The most recent Workshop to cluster antigens and thus antibodies thereto was held in Vienna in February 1989. The most recent list of cluster designations has been published in Journal of Immunology, 143:758 (1989)).

CD16 is an antigen of approximately 50-70 kD and is an Fc receptor for IgG. Besides NK cells, CD16 is expressed on granulocytes, activated macrophages and a minor subset of T cells. Functionally, the binding of immune complexes (e.g. antibody coated target cells) or anti-CD16 monoclonal antibodies to CD16 on NK cells causes a rapid increase in intracellular Ca⁺⁺ and inositol trisphosphate (or "IP$_3$") generation with subsequent transcription of lymphokines and triggering of cell mediated toxicity.

Two highly homologous genes encode CD16. CD16-I encodes a phosphatidylinositol(PI) glycan linked glycoprotein expressed by granulocytes, whereas CD16-II encodes a transmembrane-anchored glycoprotein expressed on NK cells and on activated macrophages. The expression of CD16 II on the surface of COS-7 cells (a monkey kidney tumor cell line, ATCC CRL 1651) requires co-transfection with the $\gamma$ subunit of the high affinity IgE receptor or the CD3$\zeta$ chain.

Monoclonal antibodies can be raised against CD16 by conventional techniques such as those described by Kohler and Milstein. See Nature, 256:495 (1975). For example, mice can be immunized with large granular lymphocytes (or NK cells) isolated from human peripheral blood. Spleen cells from mice so immunized then can be hybridized to a mouse plasmacytoma cell line, such as P3-X63 (ATCC TIB 9), in the presence of a agent such as polyethylene glycol. Clones then can be screened for reactivity with NK cells. Anti CD16 monoclonal antibodies are commercially available from Becton Dickinson Immunocytometry Systems (or "BDIS") as Anti-Leu 11.

CD56 is an antigen of approximately 145-220 kD. It is expressed on essentially all resting and activated NK cells, on approximately 5% of T cells but not on granulocytes, monocytes or B cells. Anti-CD56 monoclonal antibodies can be prepared as above using the KG-1a cell line (a human hematopoietic cell line, ATCC CCL 246.1) as an immunogen. Commercially, an anti-CD56 monoclonal antibody is available from BDIS as Anti-Leu 19.

Not all NK cells, however, express CD16. Similarly, there are NK cells that express quantitatively less CD56. Using anti-CD16 and anti-CD56 monoclonal antibodies which have been fluorescently labelled by conventional techniques with chromophores such as phycoerythrin and fluorescein isothiocyanate in combination with a flow cytometer, three distinct subsets of NK cells are found: 1) a small population of CD56$^{bright}$, CD16$^{negative}$ cells; 2) a small population of CD56$^{bright}$, CD16$^{dim}$ cells; and 3) a major population of CD56$^{dim}$, CD16$^{bright}$ cells ("Bright" and "dim" refer to the fluorescence intensity of the cell stained with a labelled monoclonal antibody. The cells that express the most antigen will be "bright", those that express less antigen will be "dim" and those that express no antigen will be "negative.") These populations are referred to as CD16⁻, CD16hu + and CD16⁺⁺ NK cells, respectively. The CD16⁺⁺ population comprises ~15% of total peripheral blood lymphoctyes (or "PBL") while the CD16⁺ and CD16⁻ populations comprise less than 1% of PBL. It is thought that CD16⁺ cells eventually become CD16⁺⁺.

Besides expressing CD16 and CD56, NK cells also express a variety of other antigens including CD2, CD7, CD11b, CD38, CD45R, CD18 and the p75 subunit of the interleukin 2 receptor (or "IL 2R"). A minor population of NK cells also express low surface density CD8. None of the CD16⁻, CD16⁺ or CD16⁺⁺ NK cell populations express on their cell surface CD3 $\gamma$, $\delta$ or $\epsilon$ or react with antibodies that preferentially bind the $\alpha$/$\beta$ or $\gamma$/$\delta$ subunits of TcR. Additionally, none of the populations react with antibodies against T cell associated antigens CD4, CD5 or CD28, the B cell associated antigen CD19 or the monocyte associated antigen CD14.

There are, however, differences between the three populations of NK cells. For example, 50-60% of the CD16⁺⁺ NK cells express CD57, but neither the CD16⁺ nor the CD16⁻ NK cell populations generally express CD57. On the other hand, both the CD16⁻ and CD16⁺ populations express a high surface density of Leu-8 (a 70-80 kD antigen that the BDIS monoclonal antibody Anti Leu-8 reacts with on the majority of PBL, thymocytes and B cells and which was prepared using peripheral blood T cells as an immunogen) but only 20% of CD16⁺⁺ NK cells also express Leu-8. Further, CD16⁺⁺ NK cells express no CD25 but the CD16⁺ and CD16⁻ NK cell populations express detectable levels of CD25.

Functionally, CD16⁻ NK cells isolated directly from blood have little cytolytic activity against human tumor cell targets such as K-562 (ATCC CCL 243). CD16⁻ and CD16⁺⁺ NK cells both show cytolytic activity against NK sensitive tumor cell targets with the CD16⁺⁺ NK cells showing a greater activity. On the other hand, CD16⁻ and CD16⁻ NK cells have a greater proliferative response to IL-2 than do CD16⁺⁺ cells.

Taken together, the several NK cell populations appear to comprise a continuum of differentiation in the peripheral blood with the CD16⁻ population being the most immature and the CD16⁺⁺ population being the most mature. Accordingly, in adoptive immunotherapy, such as that described in U.S. Pat. No. 4,607,007, it may be more appropriate to use CD16⁻ or CD16⁺ NK cells to achieve a greater effect.

Apart from this characterization of NK cells, other work has been done to determine how NK cells recognize a target cell in the absence of the MHC. As previously described, T cells can function in a cytolytic manner but usually do so only in the context of the MHC. It is believed that the recognition function by the T cell is mediated through the TcR but that signal transduction to turn on the cells cytolytic function occurs through the co associated CD3 structure via the PI pathway.

The T cell antigen receptor is composed of an α/B or γ/δ TcR heterodimer that is non-covalently associated with CD3. CD3 is a complex of at least five subunits, designated CD3γ, δ, ε, ζ and η. CD3γ, δ, ε, ζ are monomeric proteins encoded by genes closely-linked on chromosome 11, whereas CD3ζ is on chromosome 1 and expressed as a disulfide linked homodimer or a heterodimer in association with CD3η. Antigen induced T cell activation results in tyrosine phosphorylation of CD3ζ. It is believed that efficient signal transduction via the CD3/TcR complex requires expression of CD3ζ.

Because NK cells lack surface CD3 γ, δ and ε and TcR, there has been interest in determining how recognition occurs and how signal transduction occurs. Recently, it has been reported by Anderson et al., Nature, 341:159 (1989), that CD3ζ is expressed on NK cells. Anderson et al. further reported that there were apparently novel structures associated with CD3ζ. In FIG. 4, they show 12 kD, 60-70 kD and 80-90 kD proteins all associated with CD3ζ. Surprisingly, however, it has been discovered that the 60-70 kD structure is not novel but is, in fact, CD16. Thus, there is little information to suggest through what mechanism signal transduction occurs in NK cells that lack CD16.

SUMMARY OF THE INVENTION

The present invention comprises a novel structure co-associated with CD3ζ on NK cells. The structure comprises a protein complex of approximately 50 kD and which may be isolated in purified form.

The present invention further comprises monoclonal antibodies directed against the protein complex and methods of using the protein complex as an immunogen to produce monoclonal antibodies against it.

The present invention still further comprises a method of detection of hematopoietic cells bearing the protein complex.

The present invention also comprises a method for killing tumor targets by NK cells using an effective amount of a monoclonal antibody or antibodies against the protein complex in vivo.

DETAILED DESCRIPTION

The present invention relates to a novel protein complex designated p50. To elucidate this structure, the relationship between CD3ζ and CD16⁺ on NK cells was examined first.

The IL-2 dependent NK cell line was used as a source of NK cells having the phenotype CD3ε⁻, CD56⁺. (This cell line was established in cell culture conditions as described by Yssel et al., J. Immunol. Meth., 72:219 (1984)). As a control, granulocytes obtained from peripheral blood also were used. The cells were labelled with ¹²⁵I as described in Lanier et al., J. Exp. Med., 165:1076 (1987). (Note that CD3ζ does not contain tyrosine residues exposed on the cell surface; therefore, CD3ζ should not be labelled efficiently by the ¹²⁵I ) After labelling, the cells were lysed in 10 mM Tris and 150 mM NaCl (pH 7.2 containing 1% digitonin (CalBiochem), 1 mM PMSF (phenyl methyl sulfonyl fluoride) and 20 KU/ml aprotinin (Sigma)). These conditions were used to preserve the non covalent associations of membrane protein complexes.

Nuclei were removed by centrifugation at 13,000×g for 5 minutes. Cell lysates were precleared three times with 10 mg Pansorbin ™ (Protein A, CalBiochem-Behring) coated with saturating amounts of rabbit anti-mouse Ig serum. Antigens were immunoprecipitated with Pansorbin ™ precoated with control rabbit Ig, rabbit anti-CD3ζ (provided by L. Samelson, National Institutes of Health) or anti-CD16 (clone CLB-FcGranl, provided by P. Tetteroo and T. Huizinga, Amsterdam).

The structure precipitated by the anti-CD3ζ antibody further was eluted from the immunoabsorbant by incubation for 3 hours at 4° C. in 200 μl of 50 mM Tris and 150 mM NaCl (pH 8 containing 1.5% NP 40 (Nonidet P 40) and protease inhibitors). The eluted material was re immunoprecipitated with Pansorbin ™ coated with control Ig or anti-CD16. See FIG. 1C.

Samples of all cell lysates were denatured in sample buffer containing 5% 2 mercaptoethanol, and then were analyzed by sodium dodecylsulfate polyacrylamide gel electrophoresis (or "SDS-PAGE", 10% acrylamide). An autoradiograph of the gels then was made.

Figure 1:
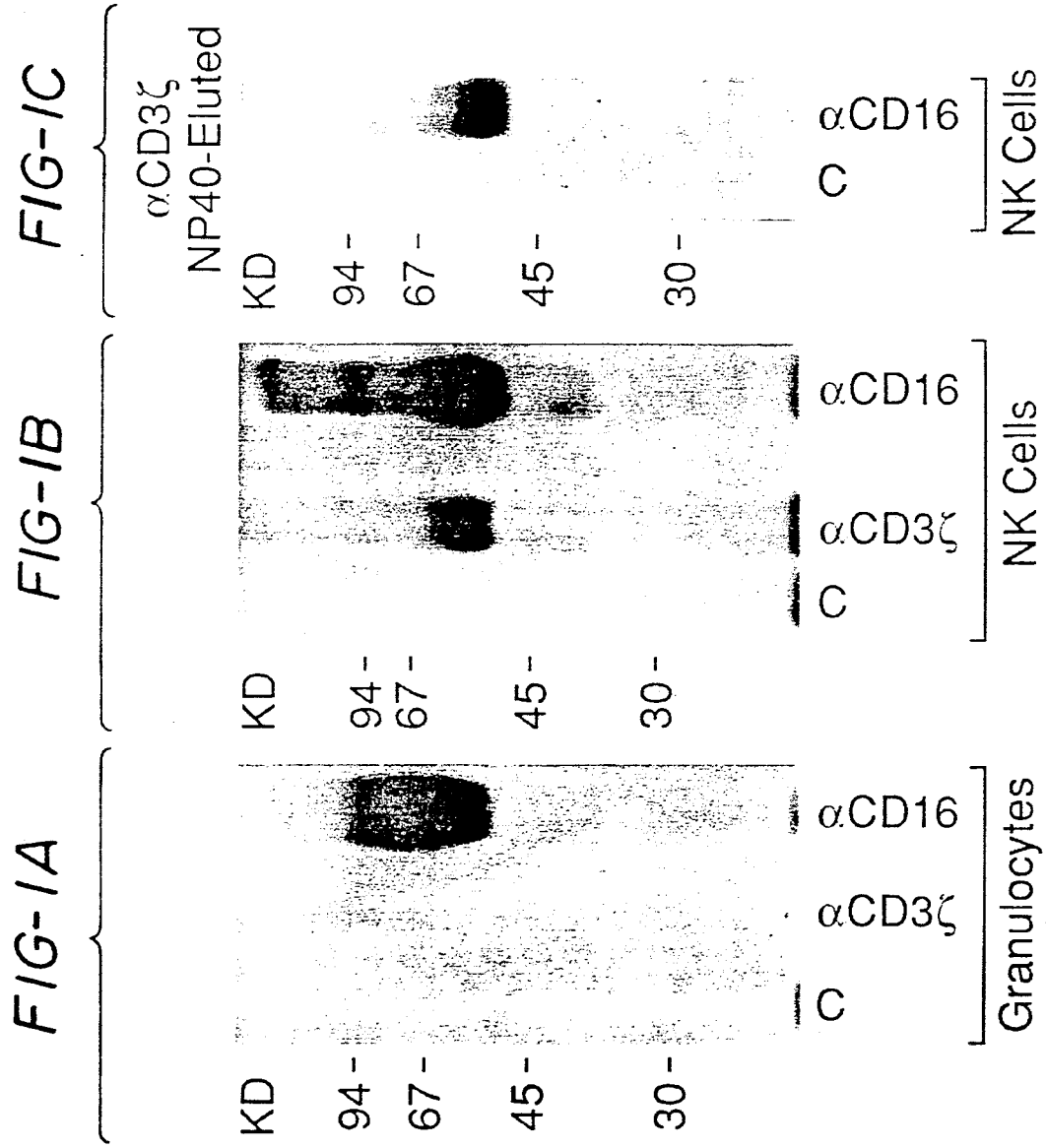
FIG. 1 comprises a series of autoradiographs of acrylamide gels of granulocytes (A) and NK cells (B C) that have been labelled with ¹²⁵I and subsequently immunoprecipitated with either a rabbit Ig control, anti-CD3ζ antibody or anti-CD16 antibody.

Referring to FIG. 1A, samples of granulocyte lysates immunoprecipitated with rabbit Ig (or "C"), anti-CD3ζ or anti-CD16 were run. As expected, CD16 was bound by the anti-CD16 antibody in the lysates while neither the control nor anti-CD3ζ lanes showed any reactivity.

Referring to FIG. 1B, samples of the NK cell lysates immunoprecipitated with rabbit Ig, anti-CD3ζ or anti-CD16 were run. The lanes of both the anti-CD3ζ and anti-CD16 bound lysates show a structure between 50–70 kD. Referring to FIG. 1C, it is evident that the 50–70 kD structure that co-precipitated with CD3ζ is CD16 and not some other novel structure as reported by Anderson et al., supra.

Figure 2:
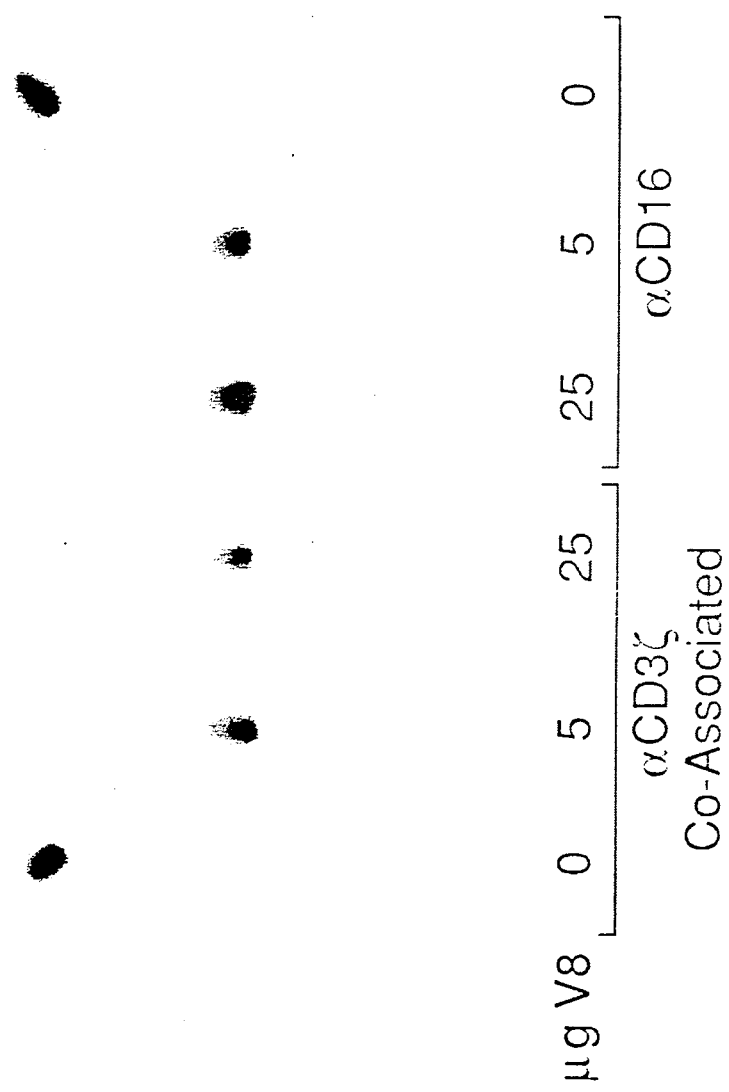
FIG. 2 comprises an autoradiograph of an acrylamide gel of the 50-70 kD bands taken from FIG. 1B which then were reacted with various amounts of S. aureus protease V8.

To confirm this point, the 50–70 kD bands from FIG. 1B were cut from the lanes. They then were separately digested for 1 hour with 0, 5 or 25 μg of S. aureus V8 protease (Sigma) and analyzed by SDS PAGE (15% acrylamide). Referring to FIG. 2, the bands cut from the anti-CD3ζ and anti-CD16 lanes cut from FIG. 1B both show essentially identical peptides further indicating that the 50–70 kD structure non covalently bound to CD3ζ is CD16.

To confirm that CD3ζ was, in fact, being expressed by the NK cell line used, the NK cell line described above was metabolically labelled for 18 hours in methionine and cysteine free RPMI-1640 ™ (a cell culture media (Gibco)) containing 0.2 mCi/ml $^{35}$S-methionine and cysteine (Trans $^{35}$S label, ICN), 25 mM HEPES (pH 7.4), gentamicin and 5% dialyzed fetal calf serum (or "FCS"). Cells were lysed in 50 mM Tris and 150 mM NaCl (pH 8 containing 1% NP-40, 1 mM PMSF and 20 KU/ml aprotinin) for 20 minutes at 4° C. Nuclei were removed as above. Lysates were immunoprecipitated with either control rabbit Ig or anti-CD3ζ. Samples were analyzed by two dimensional diagonal SDS PAGE (1st dimension non-reducing; 2nd dimension reducing; 12.5% acrylamide).

Figure 3B:
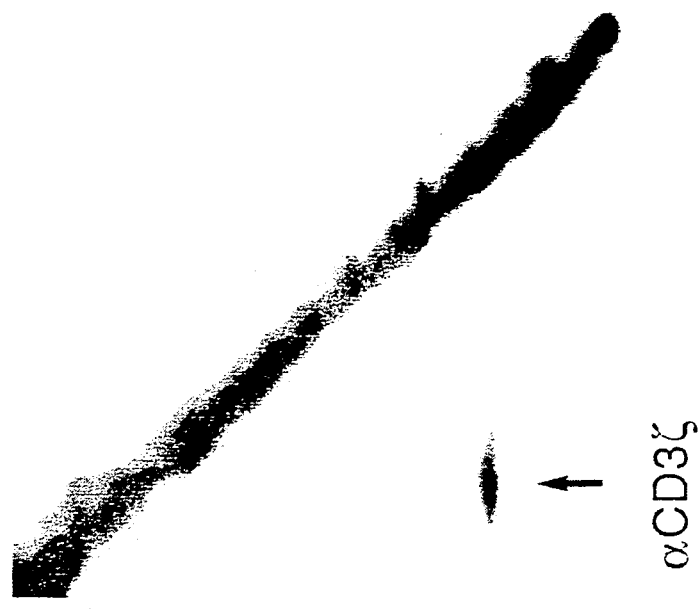
FIG. 3 comprises an autoradiograph of a two dimensional acrylamide gel (1st dimension non reducing, 2nd dimension reducing) of NK cells labelled with ³⁵S methionine and cysteine and subsequently immunoprecipitated with a rabbit Ig control (A) or anti-CD3ζ antibody (B).
Figure 3A:
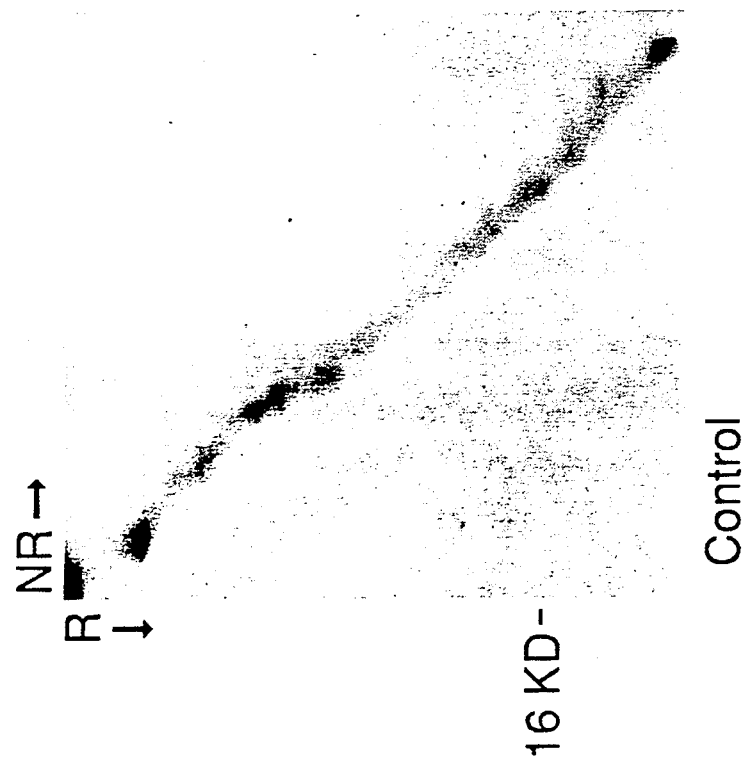

Referring to FIG. 3A, it can be seen that the rabbit Ig does not precipitate any off diagonal structure from the lysates. In FIG. 3B, however, the characteristic CD3ζ disulfide linked homodimer was elucidated at 16 kD.

Given the role of CD3ζ in activation through the TcR, it is likely that CD3ζ is involved in signal transduction via transmembrane anchored CD16. The requirement for the CD3ζ homodimer for expression of CD16 in NK cells is analogous to the requirement for the γ homodimer for the expression of the high affinity IgE receptor (FcR) present on mast cells and basophils. It is noted that the transmembrane segment of γ FcR subunit is highly homologous to the CD3ζ transmembrane segment suggesting that the interaction site is between residues in the transmembrane segments of CD3ζ and CD16. The results indicate that CD3ζ or a family of homologous structures may co associate with membrane receptors involved in signal transduction in several different cell types. The issue that is left open, however, is how signal transduction is achieved in CD16⁻ NK cells.

CD16⁻ NK cells were isolated from normal peripheral blood by purifying CD16⁻, CD56⁺ lymphocytes. The cells then were labelled with $^{125}$I as above and lysates were prepared as above. The lysates then were immunoprecipitated with rabbit Ig, anti-CD3ζ and anti-CD16 as above. The lysates then were subjected to SDS-PAGE (12.5% acrylamide) as above.

Figure 4B:
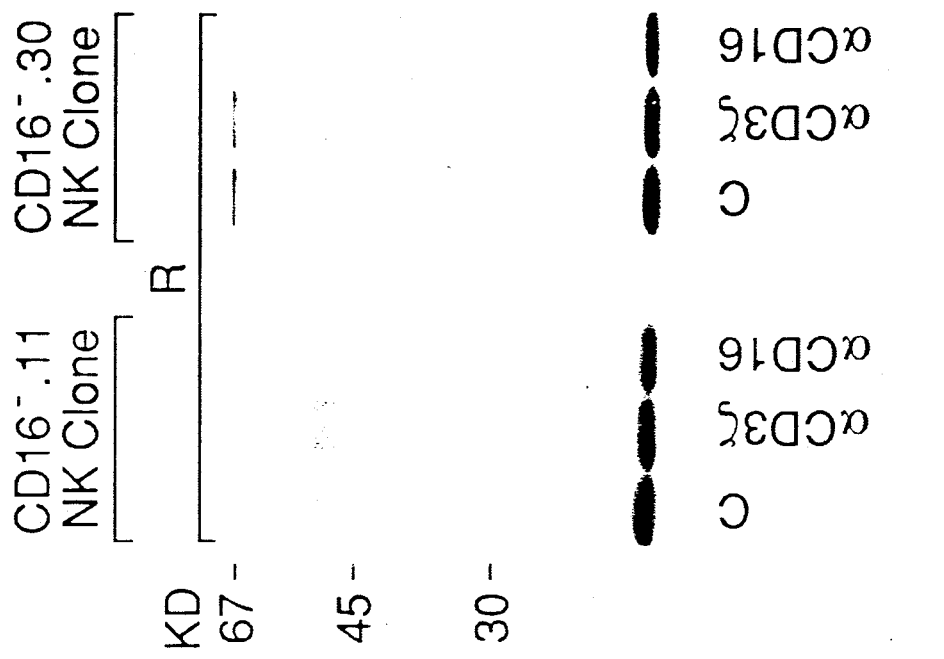
FIG. 4 is an autoradiograph of an acrylamide gel of CD16⁺ NK cells (A) and CD16⁻ NK cells (B) labelled with 125I and immunoprecipitated with a rabbit Ig control, anti-CD3ζ and anti-CD16.
Figure 4A:
Figure 5:
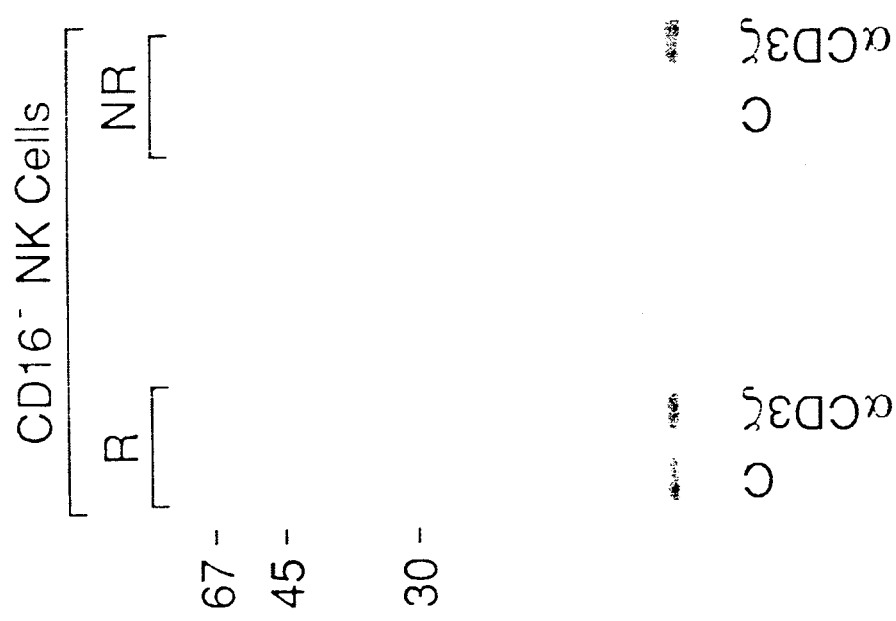
FIG. 5 is an autoradiograph of an acrylamide gel of CD16⁻ NK cells labelled with ¹²⁵I and immunoprecipitated with a rabbit Ig control and anti-CD3ζ under (A) non reducing and (B) reducing conditions.

Referring to FIG. 4B, it can be seen that neither the control nor the anti-CD16 lanes show any specific reactivity. The anti-CD3ζ lane, however, shows the 16 kD structure of CD3ζ but also shows a 50 kD complex not previously seen. This complex has been named p50. In FIG. 4A, the p50 protein does not appear indicating the probable absence of the complex on CD16⁺ NK cells. FIG. 5 confirms that the p50 protein complex is stable under both reducing (B) and non reducing conditions (A).

To purify the p50 protein complex, labelled CD16⁻ NK cells, such as those described above, can be used. Using an anti-CD3ζ antibody, the p50 protein can be isolated by co-precipitation. The protein then can be eluted from anti-CD3ζ, concentrated and purified. Alternatively, lysates of CD16⁻ cells can be prepared and the p50 protein can be eluted from gels of anti-CD3ζ co-precipitates. The p50 protein complex can be separated by using conventional protein sequencing methods, as described in Protein Sequencing: A Practical Approach, IRL Press, (Findlay et al., ed.s, 1989), for example, and oligonucleotide proteins constructed from the derived polypeptide sequence in order to isolate the gene for p50.

In another embodiment, mRNA corresponding to the p50 protein can be isolated from CD16⁻ by density dependent centrifugation. Once the mRNA is isolated, cDNA can be prepared from it by using reverse transcriptase under the appropriate conditions and inserted into an appropriate phage or plasmid vector. The cDNA encoding proteins of the p50 complex can be isolated by several strategies including, but not restricted to, screening bacterial expression systems (e.g., λgt11, Stratagene) or mammalian expression systems (e.g., CDM8, Invitrogen) using antibodies against the p50 protein complex. See generally Molecular Cloning: A Laboratory Manual (2nd ed.), Cold Spring Harbor Laboratory Press (Sambrook, Fritsch and Maniatis eds., 1989).

Once the sequence of the cDNA is known, the amino acid composition of the p50 protein complex can be determined.

There are several options available for making an antibody that will bind to the p50 protein. In one embodiment, p50 complex proteins purified by any of the methods set forth above can be used to immunize mice, rabbits, rats or other animals to raise antisera to p50 complex. In the more preferred embodiment, monoclonal antibodies that will bind to the p50 protein can be prepared. In this embodiment, mice are immunized with cells bearing p50 or more preferredly with purified p50. The spleens are removed after a period of time and spleen cells are fused with an immortal mouse plasmacytoma cell line, such as SP2/0 (ATCC CRL 1581) or P3X63 in the presence of a fusion agent, such as polyethylene glycol. The resulting hybridomas then can be screened for reactivity of their supernatants with purified p50 or cells expressing the p50 complex. Hybridomas producing monoclonal antibodies that bind to p50 can be cloned for further analysis of their reactivities.

The antibodies produced as described above that bind to p50 can then be used in a diagnostic assay to identify and isolate p50 bearing cells. In one method, the antibodies can be labelled with an enzyme, such as horseradish peroxidase, a fluorescent dye, such as a phycobiliprotein, or a radioisotope, such as $^{125}$I. Cells binding to the labelled antibody can then be detected by conventional methods, such as flow cytometry or gamma counting. In a more preferred method, the antibody is a monoclonal antibody and the label is a fluorescent dye. The fluorescent dye can be directly conjugated to the antibody by means such as those described in U.S. Pat. No. 4,520,110 for phycobiliproteins, U.S. Pat. No. 4,876,190 for peridinin chlorophyll complex, or if the monoclonal antibody is made in a mouse it can be detected using a labelled goat or rabbit anti-mouse antibody as a second step reagent. In the preferred method, cells that express p50 are detected by means of a flow cytometer, such as that described in U.S. Pat. No. 4,599,307 or 4,745,285.

Given that CD16+ NK cells can be activated using antibodies against the CD3ζ co associated CD16 protein, it also may be possible to use an antibody that binds to p50 to stimulate such activity in CD16− NK cells either in vitro or in vivo. The dose of administration of the antibodies can be in an amount sufficient to activate the p50 bearing cells. In this method, it is preferred that the antibodies be monoclonal and more preferably be chimeric for in vivo applications, such as those described in U.S. Pat. No. 4,816,397 or GB Pat. Appl. No. 2 188 638 A (published Oct. 7, 1987). It is to be appreciated that the antibody also can be used to isolate p50 bearing cells from peripheral blood. In this method, IL-2 (or another immune stimulator, e.g., interferon) can be used to activate the isolated cells in vitro before being returned to the body. Alternatively, peripheral blood containing p50 bearing cells can be activated in vitro using the antibodies.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. An antibody that specifically binds to an epitope on a protein, said protein having a molecular weight of approximately 50kD, and said protein being associated on CD16− NK cells with CD3ζ.

2. The antibody of claim 1 wherein the antibody is a monoclonal antibody.

3. A method of detecting cells bearing a protein having a molecular weight of approximately 50 kD and which is associated on CD16− NK cells with CD370 comprising the steps of reacting cells in a sample with an antibody specifically that binds to said 50 kD protein, labelling the antibody with a detectable label and detecting the presence or absence of the label on said cells.

4. The antibody of claim 3 wherein the antibody is a monoclonal antibody.

5. The method of claim 3 wherein the antibody is labelled directly prior to reacting the cells with said antibody.

6. The method of claim 3 wherein the label is a radioisotope, fluorescent dye or enzyme.

7. The method of claim 6 wherein the label is a fluorescent dye and fluorescence is detected by means of flow cytometry.

* * * * *